United States Patent [19]
Herrnstadt et al.

[11] Patent Number: 4,797,276
[45] Date of Patent: Jan. 10, 1989

[54] COTTON BOLL WEEVIL, ALFALFA WEEVIL, AND CORN ROOTWORM VIA CONTACT WITH A STRAIN OF BACILLUS THURINGIENSIS

[75] Inventors: Corinna Herrnstadt; George G. Soares, both of San Diego, Calif.

[73] Assignee: Mycogen Corporation, San Diego, Calif.

[21] Appl. No.: 842,529

[22] Filed: Mar. 21, 1986

Related U.S. Application Data

[63] Continuation-in-part of Ser. No. 714,790, Mar. 22, 1985, Pat. No. 4,764,372.

[51] Int. Cl.⁴ ............... C12P 21/00; C12R 1/07; A01N 63/00
[52] U.S. Cl. .................................. 424/84; 424/93; 435/68; 435/832
[58] Field of Search .............. 435/253, 68, 832; 424/84, 92, 93

[56] References Cited

U.S. PATENT DOCUMENTS 3,086,922  4/1963  Mechalas ..................... 435/253

FOREIGN PATENT DOCUMENTS 0149162  12/1984  European Pat. Off. ......... 424/93

OTHER PUBLICATIONS

Cantwell et al., "Activity of the $\beta$-Exotoxin of *Bacillus thuringiensis* Var. *Thuringiensis* Against the Colorado Potato Beetle", *Biol. Abst.*, vol 77, N. 8 (4-15-1984).
Cantwell et al.; "Control of the Colorado Potato Beetle with *Bacillus thuringiensis* Var. *Thuringiensis*"; *Biological Abstracts*, vol. 79, N. 3 (2-1-1985).
Galani et al.; "Studies on the Histopathological Changes Induced in the Colorado Potato Beetle by $\beta$-Exotoxin of *Bacillus thuringiensis* Berlines"; *Chem. Abst.*, Vol. 89, N. 19 (1978); Abst. 158714h.
Wilson et al.; "Susceptibility of the Alfalfa Weevil to a *Bacillus thuringiensis* Exotoxin"; *Biol. Abstr;* vol. 79, No. 1, (1-1-85).
Ignoffo et al.; "Susceptibility of the Colorado Potato Beetle *Leptinotarsa decemlineata* to *Bacillus thuringiensis*"; *J. Invert. Path.*, vol. 39, pp. 244–246, (1982).
Beegle, C. C. (1978) "Use of Entomogenous Bacteria in Agroecosystems," Developments in Indust. Microbiol. 20:97–104.
Couch, T. L., (1980), "Mosquito Pathogenicity of *Bacillus thuringiensis* Var. *Israelensis,*" Dev. in Indust. Microbiol. 22:61–67.
Krieg, A. et al., (1983), "*B. thuringiensis* Var. *Tenebrionis*: A New Pathotype Effective Against Coleoptera Larvae," Z. Ang. Ent. 96:500–508. (In German and English).

Primary Examiner—Elizabeth C. Weimar
Attorney, Agent, or Firm—Roman Saliwanchik; David R. Saliwanchik

[57]  ABSTRACT

The subject invention concerns a novel and useful insecticide with activity against insect pests of cotton, potato, alfalfa and corn crops. these pests do heavy damage to the crops. The insecticide of the subject invention is a *B. thuringiensis* microbe given the designation strain san diego. The spores or crystals of this microbe are useful to control the cotton boll weevil, the Colorado potato beetle, the alfalfa weevil, and the corn rootworm.

6 Claims, No Drawings

COTTON BOLL WEEVIL, ALFALFA WEEVIL, AND CORN ROOTWORM VIA CONTACT WITH A STRAIN OF BACILLUS THURINGIENSIS

This is a continuation-in-part application of our co-pending application U.S. Ser. No. 714,790, filed Mar. 22, 1985, now U.S. Pat. No. 4,764,372.

DESCRIPTION

Background of the Invention

*Bacillus thuringiensis* (Bt) produces an insect toxin designated as δ-endotoxin. It is synthesized by the Bt sporulating cell. The toxin, upon being ingested in its crystalline form by susceptible insect larvae, is transformed into biologically active moieties by the insect gut juice proteases. The primary target is insect cells of the gut epithelium, which are rapidly destroyed.

The reported activity spectrum of Bt covers insect species within the order Lepidoptera, many of which are major pests in agriculture and forestry. The activity spectrum also includes the insect order Diptera, which includes mosquitoes and black flies. See Couch, T. L., (1980) "Mosquito Pathogenicity of *Bacillus thuringiensis* var. *israelensis*," Developments in Industrial Microbiology 22 :61–76 Beegle, C. C., (1978) "Use of Entomogenous Bacteria in Agroecosystems," Developments in Industrial Microbiology 20:97–104. Krieg, et al., Z. ang. Ent. (1983) 96:500–508, describe a Bt isolate named *Bacillus thuringiensis* var. *tenebrionis,* which is reportedly active against two beetles in the order Coleoptera. These are Colorado potato beetle, *Leptinotarsa decemlineata,* and *Agelastica aini.*

In our parent application, Ser. No. 714,790, we disclose a novel Bt isolate active against Coleoptera. There is no disclosure of activity against the cotton boll weevil (*Antnonomus grandis*), tne Colorado potato beetle (*Leptinotarsa decemlineata*), the alfalfa weevil (*H-ypera postica*) or the corn rootworm (*Diabrotica longicornis*). We have also subsequently discovered that this Bt isolate is not active against all Coleoptera tested. See Table 1, infra.

COTTON BOLL WEEVIL

The cotton boll weevil is easily one of the most notorious agricultural pests in the world. It occurs in all the principal cotton growing areas of Central and South America and the United States except parts of California. Wherever it is presant it is the key pest in cotton. The injury is caused by the adults and the larvae or grubs. The adult weevils chew into or puncture the squares and bolls, and with their long slender bills, feed on the inner tissues. The eggs are laid in these holes and the hatching grubs bore into the boll or square, causing the squares to drop off or wither and dry on the plant. This feeding either results in direct destruction of the flower or reduction of fiber content in the boll. Losses can be so great as to be limiting. In 1982 damage to cotton in the U.S. was estimated at $429 million. This figure is expected to continue to increase.

Chemical insecticides and cultural controls are currently empoyed in the control of boll weevil. These have associated problems and are not completely effective. There is a definite need for alternative materials that could be used in a complementary fashion with existing controls and to replace control agents that may lose efficacy due to resistance or other factors.

COLORADO POTATO BEETLE

The Colorado potato beetle (CPB) is the most important defoliating insect pest of potatoes worldwide and is of particular importance in the northeastern United States, Europe and the Soviet Union. In the U.S. it is a key insect pest of potatoes in all the majrr potato-producing areas of the U.S. except California. This is an area representing 750,000 acres of potatoes. This species is also a serious pest on eggplant, tomato, and pepper.

Both the adults and larvae feed on the foliage. In most areas, two to three generations occur each year. If left unchecked this pest can severely defoliate a crop, often consuming all of the above-ground portions of the host plant.

Chemical pesticides are used to control this pest: however, one of the principal problems in the use of this strategy is the ability of the beetle to rapidly develop resistance to new chemical insecticides. Generally 2 to 10 applications of insecticide are made to control CPB, depending on the levels of insecticide resistance, population density and number of generations per year. Resistance to virtually all available insecticides has been documented in some areas, notably Long Island, N.Y. This has made it practically impossible to grow potatoes in these areas. All of this indicates the urgency of finding new agents for the control of CPB, particularly agents that have a mode of action very different from the conventional insecticides currently being used. The Bt strain described here is such an agent. It acts as a proteinaceous stomach poison as opposed to a contact nerve poison. The importance of CPB and the urgency of finding insecticides to which this pest is not resistant make it imperative that new insecticidal agents like the strain described herein be developed as rapidly as possible.

ALFALFA WEEVIL

The alfalfa weevil, *Hypera postica,* and the closely related Egyptian alfalfa weevil, *Hyoera brunneipennis,* are the most important insect pests of alfalfa grown in the United States, with 2.9 million acres infested in 1984. An annual sum of 15 million dollars is spent to control these pests. The Egyptian alfalfa weevil is the predominant species in the southwestern U.S., where it undergoes aestivation (i.e., hibernation) during the hot summer months. In all other respects, it is identical to the alfalfa weevil, which predominates throughout the rest of the U.S.

The larval stage is the most damaging in the weevil life cycle. By feeding at the alfalfa plant's growing tips, the larvae cause skeletonization of leaves, stunting, reduced plant growth, and, ultimately, reductions in yield. Severe infestations can ruin an entire cutting of hay. The adults, also foliar feeders, cause additional, but less significant, damage.

Chemical insecticides play a major role in effective alfalfa weevil control. However, there are several problems associated with their use including:

1. acute mammalian toxicity: several of the most effective insecticides used for weevil control are highly toxic to humans and other mammals, and are sold on a restricted basis in many states. Toxic residues are an additional problem for hay sold as feed for livestock.

2. honeybee toxicity: the honeybee is sensitive to some of the insecticides used for alfalfa weevil control. Because alfalfa is the major source of nectar for commercial honeybee colonies in the U.S., the use of insecticides with honeybee toxicity is incompatible with the needs of the honey producers.

3. toxicity to natural enemies: the insect parasites and predators which normally help control populations of minor alfalfa pests (aphids, leafhoppers, caterpillars) are highly susceptible to all insecticides presently used for alfalfa weevil control. Reductions in the numbers of beneficial insects can result in increased populations of these once minor pests, and in the consequent application of additional insecticides.

CORN ROOTWORM

Approximately 9.3 million acres of U.S. corn is infested with the corn rootworm species complex, which includes the northern corn rootworm, *Diabrotica longicornis*, the southern corn rootworm, *D. undecimpunctata*, and the western corn rootworm, *D. virgifera*. The soil-dwelling larvae of these *Diabrotica* species feed on corn root, causing lodging of the corn plant. This eventually results in yield reduction or death of the plant. By feeding on cornsilks the adults reduce pollination and, therefore, the yield of corn per plant. In addition, adults and larvae of the southern corn rootworm, also known as the spotted cucumber beetle, attack cucurbit crops (cucumbers, squash, melons, etc.) and many vegetable and field crops in commercial production, as well as in home gardens.

Control of the corn rootworm has been partially addressed by cultural methods, such as crop rotation and application of high nitrogen levels to stimulate the growth of adventitious root systems. However, chemical insecticides are relied upon heavily to guarantee the desired level of control. Insecticides are banded onto the soil or incorporated into the soil. The major problem associated with the use of these chemicals is the development of resistance among the treated insect populations.

BRIEF SUMMARY OF THE INVENTION

Disclosed and claimed is the use of our *Bacillus thuringiensis* isolate to control the cotton boll weevil (*Anthonomus grandis*), the Colorado potato beetle (*Leptinotarsa decemlineata*), the alfalfa weevil (*Hypera postica*) and the corn rootworm (*Diabrotica longicornis*). This *B. thuringiensis* isolate, initially designated "M-7", has now been named *B. thuringiensis* strain *san diego*. (*B.t.sd*).

Because the boll weevil and the Colorado potato beetle are not iniigenous to California, we have developed a bioassay using the elm leaf beetle (*Pyrrhalta luteola*). Both adults and larvae of this species show greater than 90% mortality when exposed to host plant leaves treated with *B.t.sd* spore/crystal preparations at $10^4$ spore equivalents per square centimeter of leaf surface. In contrast, treatment of these insects with the lepidopteran-specific strain of *Bacillus thuringiensis* HD-1 at $10^6$ spore equivalents/cm$^2$ gave less than 5% mortality.

*B.t.sd* has shown significant levels of activity against larvae of the Egyptian alfalfa weevil and the southern corn rootworm.

DETAILED DISCLOSURE OF THE INVENTION

The *Bacillus thuringiensis* isolate used in the subject invention, designated *B.t.sd*, is unusual in having a unique parasporal body (crystal) which under phase contrast microscopy is dark in appearance with a flat, square configuration.

A subculture of *B. thuringiensis* strain *san diego* has been deposited in the permanent collection of the Northern Regional Research Laboratory, U.S. Department of Agriculture, Peoria, Ill., U.S.A. on Feb. 27, 1985. The culture was assigned the accession number NRRL B-15939 by the repository. This deposit is available to the public upon the grant of a patent disclosing it. The deposit is also available as required by foreign patent laws in countries wherein counterparts of the subject application, or its progeny, are filed. However, it should be understood that the availability of a deposit does not constitute a license to practice the subject invention in derogation of patent rights granted by governmental action. *B. thuringiensis* strain *san diego*, NRRL B-15939, can be cultured using standard art-media and fermentation techniques. Upon completion of the fermentation cycle the bacteria can be harvested by first separating the Bt spores and crystals from the fermentation broth by means well known in the art. The recovered Bt spores and crystals can be formulated into a wettable powder, liquid concentrate, granules or other formulations by the addition of surfactants, dispersants, inert carriers and other components to facilitate handling and application for particular target pests. These formulation and application procedures are all well known in the art and are used with commercial strains of *B. thuringiensis* (HD-1) active against Lepidoptera, e.g., caterpillars.

Formulated products can be sprayed or applied onto foliage to control phytophagous beetles, or formulated bait granules containing an attractant and spores and crystals of *B.t.sd* can be applied to the soil. Formulated *B.t.sd* can also be applied as a seed-coating or root treatment or total plant treatment at late stages of the crop cycle.

Following are examples which illustrate procedures, including the best mode, for practicing the invention. These examples should not be construed as limiting. All percentages are by weight and all solvent mixture proportions are by volume unless otherwise noted.

EXAMPLE 1

Culturing *B. thuringiensis* strain *san diego* NRRL B-15939.

A subculture of *B. thuringiensis* strain *san diego* NRRL B-15939 can be used to inoculate the following

| Tryptone | 10 gm |
| Yeast extract | 5 gm |
| NaCl | 5 gm |
| 5 N NaOH | 0.6 ml |
| Water | 1000 ml |

As per standard microbiological techniques, the above medium would be sterilized prior to inoculation and the inoculation would be done using aseptic procedures.

A procedure that has produced good results is as follows:

A series of 150 ml Erlenmeyer flasks containing sterila PWYE medium (peptone 5.0%; yeast extract 0.1%: NaCl 0.5% in 1 liter of water: adjust pH to 7.5) are inoculated from a petri plate culture of *B. thuringiensis* M-7, NRRL B-15939. The flasks are incubated at 30° C. on a rotary shaker (200 rpm) overnight. From this starter culture, 300 ml of LB broth in a 2 liter flask is inoculated using 7.5 ml of the starter. The LB-broth flasks are incubated under the same conditions as the stater, but are harvested after 4 days.

The above procedure can be readily scaled up to large fermentors by procedures well known in the art.

The Bt spores and crystals, obtained in the above fermentation, can be isolated by procedures well known in the art. A frequently-used procedure is to subject the harvested fermentation broth to separation techniques, e.g., centrifugation.

EXAMPLE 2

Testing of *B. thuringiensis* strain *san diego* NRRL B-1593Spores and Crystals

*B. thuringiensis* strain *san diego* NRRL B-15939 spores and crystals,obtained as described above, were tested against various insects by use of the following procedures: Assays against *Diabrotica undecimpunctata undecimpunctata, Leptinotarsa decemlineata* and *Pyrrhalta luteola* were carried out by spraying spore/crystal preparations, or purified crystals,onto leaf discs from appropriate host plants. Assays against *Aedes aegypti* were performed by adding spore/crystal preparations to larvae in water. All other assays were carried out by incorporating spore/crystal preparations, or purified crystals, into an appropriate standard diet mixture. More specifically, the assay for the Colorado potato beetle and the boll weevil were conducted as follows:

A. *B.t.sd* spore/crystal preparations of varying concentrations were prepared as described in Example 1. Potato leaves were dipped in these solutions, air dried for 1 hr and exposed to 2nd instar Colorado potato beetle larvae. Each dosage was tested against 20 larvae and repeated 4 times. Mortality was determined after 48 hr. The LC-50 was determined by probit analysis. This procedure yielded an LC-50 of $7.6 \times 10^6$ spores/ml of solution. LC-50 referes to a lethal concentration that kills 50% of larvae.

*B.t.sd* spore/crystal preparations of varying concentrations were prepared as described in Example 1, and incorporated into a standard boll weevil diet. Second instar boll weevil larvae were introduced to the diet and mortality was assessed after 48 hr. Each dosage of *B.t.sd* against 20 larvae and repeated 4 times. The LC-50 was determined by probit analysis (Finney, D. J. 1971 Probit Analysis 3d ed. Cambridge University Press, Cambridge). This procedure gave an LC-50 of $4.65 \times 10^5$ spores/ml of diet.

EXAMPLE 3

Activity of *B.t.sd* Against Alfalfa Weevil

*B.t.sd* spore/crystal preparations of varying concentrations were prepared as described in Example 1. Sprigs of alfalfa were dipped in these solutions and air dried for 15 min. Each sprig was then put into a small vial of water, alfalfa weevil larvae were added to the leaves, and the entire assemblage placed in an enclosed rearing chamber. Each dosage was tested against 20 2nd instar larvae and replicated 3 times. After 96 hr, the highest dosage tested, $7.6 \times 10^7$ spores/ml solution, caused 80% mortality. The surviving weevil larvae were stunted and were not feeding. Lower concentrations resulted in only minimal levels of mortality, but caused significant levels of feeding inhibition. It is likely that these feeding-inhibited larvae will not survive to adulthood in the field.

EXAMPLE 4

Activity of *B.t.sd* Against Southern Corn Rootworm

*B.t.sd* spore/crystal preparations of varying concentrations were prepared as described in Example 1. Germinated corn kernels were dipped into the solutions and air dried for 15 min. Each kernel was placed in a petri dish which contained a thin layer of sterila moist sand, and 10 2nd instar corn rootworm larvae were placed on each kernel. Each concentration was tested against 20 2nd instar larvae and replicated 3 times. After 96 hr 50% of the larvae treated at the highest dosage ($1 \times 10^{10}$) spores/ml of solution) were dead and the survivors were no longer feeding.

TABLE 1

| | | Insects Evaluated for Susceptibility to *Bacillus thuringiensis* strain san diego | | | |
|---|---|---|---|---|---|
| ORDER | FAMILY | SPECIES | COMMON NAME | STAGES TESTED | ACTIVITY |
| Coleoptera | Chrysomelidae | *Diabrotica* | Western spotted | A | — |
| | | *undecimpunctata undecimpunctata* | cucumber beetle | L | ++ |
| | | *Haltica tombacina* | | A,L | +++. |
| | | *Leptinotarsa decemlineata* | Colorado potato beetle | L | +++ |
| | | *Pyrrhalta luteola* | Elm leaf beetle | A,L | ++++ |
| | Curculionidae | *Anthonomus grandis* | Boll weevil | A | +++ |
| | | | | L | ++++ |
| | | *Otiorhynchus sulcatus* | Black vine weevil | L | ++ |
| | | *Hypera brunneipennis* | Egyptian alfalfa weevil | L | +++ |
| | Dermestidae | *Attagenus megatoma* | Black carpet beetle | L | — |
| | Ptinidae | *Gibbium psylloides* | — | A | — |
| | Tenebrionidae | *Tenebrio molitor* | Yellow mealworm | L | ++ |
| | | *Tribolium castaneum* | Red flour beetle | A,L | — |
| Diptera | Culicidae | *Aedes aegypti* | Yellow fever mosquito | L | — |
| Lepidoptera | Noctuidae | *Spodoptera exigua* | Beet armyworm | L | — |
| | | *Trichoplusia* | Cabbage looper | L | — |

TABLE 1-continued

| | Insects Evaluated for Susceptibility to *Bacillus thuringiensis* strain san diego | | | | |
|---|---|---|---|---|---|
| ORDER | FAMILY | SPECIES | COMMON NAME | STAGES TESTED | ACTIVITY |
| | | ni | | | |

Assays against *Diabrotica undecimpunctata undecimpunctata, Leptinotarsa decemlineata* and *Pyrrhalta luteola* were carried out by spraying spore/crystal preparations, or purified crystals, onto leaf discs from appropriate host plants. Assays against *Aedes aegypti* were carried out by adding spore/crystal preparations to larvae in water. All other assays were carried out by incorporating spore/crystal preparations or purified crystals into an appropriate diet mixture. Insecticidal activity was arbitrarily classified from weak (+) to very strong (++++). A: adults, L: larvae.

We claim:

1. A process, for controlling cotton boll weevil which comprises contacting the host plant of said cotton boll weevil with a cotton boll weevil-controlling effective amount of *Bacillus thuringiensis* strain *san diego,* having the identifying characteristics of NRRL B-15939, or toxic crystals or spores from said strain.

2. A process, according to claim 1, which comprises incorporating said *Bacillus thuringiensis* strain *san diego,* or toxic crystals or spores TM from said strain, into a bait granule and placing said granule on or in the soil when planting seeds of cotton, or at later stages of the crop cycle.

3. A process for controlling alfalfa weevil which comprises contacting the host plant of said alfalfa weevil with an alfalfa weevil-controlling effective amount of *Bacillus thuringiensis* strain *san diego,* having the identifying characteristics o.f NRRL B-15939, or toxic crystals or spores from said strain.

4. A process, according to claim 3, which comprises incorporating said *Bacillus thuringiensis* strain *san diego,* or toxic crystals or spores from said strain, into a bait granule and placing said granule on or in the soil when planting seeds of alfalfa, or at later stages of the crop cycle.

5. A process for controlling corn rootworm which comprises incorporating in the soil habitat of said corn rootworm a corn rootworm-controlling effective amount of *Bacillus thuringiensis* strain *san diego,* having the identifying characteristics of NRRL B-15939, or toxic crystals or spores from said strain.

6. A process, according to claim 5, which comprises incorporating said *Bacillus thuringiensis* strain *san diego,* or toxic crystals or spores from said strain, into a bait granule and placing said granule on or in the soil when planting seeds of corn, or at later stages of the crop cycle.

* * * * *

UNITED STATES PATENT AND TRADEMARK OFFICE
CERTIFICATE OF CORRECTION

PATENT NO. : 4,797,276

DATED : January 10, 1989

INVENTOR(S) : Corinna Herrnstadt, George G. Soares

It is certified that error appears in the above-identified patent and that said Letters Patent is hereby corrected as shown below:

Title: Before "COTTON" insert --CONTROL OF--.
Abstract: line 3,"these" should read --These--.
Column 1: Before "COTTON" insert --CONTROL OF--; line 26: "22:61-76" should read --22:61-76;--; line 34: "aini" should read --alni--; line 38: "Antnonomus" should read --Anthonomus--; line 38: "tne" should read --the--; line 39: "Hypera" should read --Hypera--; line 50: "presant" should read --present--.
Column 2: line 7: "majrr" should read --major--; line 16: "pest:" should read --pest;--; line 40: "Hyoera" should read --Hypera--.
Column 3: line 49: "iniigenous" should read --indigenous--; line 61: "rcotworm" should read --rootworm--.

UNITED STATES PATENT AND TRADEMARK OFFICE
CERTIFICATE OF CORRECTION

PATENT NO. : 4,797,276

DATED : January 10, 1989

INVENTOR(S) : Corinna Herrnstadt, George G. Soares

It is certified that error appears in the above-identified patent and that said Letters Patent is hereby corrected as shown below:

| | |
|---|---|
| Column 4: | line 34: "late" should read --later--; line 47: "used-to" should read --used to--; line 48: insert --medium known as LB broths:--; line 64: "0.1%:" should read --0.1%;--; line 64: "water:" should read --water;--. |
| Column 5: | line 3: "stater" should read --starter--; line 14: "B-1593Spores" should read --B-15939 Spores--; line 39: "B.t.sd." should read --B.B.t.sd.--. |
| Column 6: | lines 2-3: "B.t.sd. against" should read --B.t.sd. was tested against--. |
| Claim 2: | line 3: "spores TM from" should read --spores from--. |
| Claim 3: | line 6: "o.f" should read --of--. |

Signed and Sealed this

Twenty-third Day of May, 1989

Attest:

DONALD J. QUIGG

Attesting Officer

Commissioner of Patents and Trademarks